United States Patent
Holub et al.

(10) Patent No.: US 9,782,504 B2
(45) Date of Patent: *Oct. 10, 2017

(54) SELF-DISINFECTING SURFACE WITH PRINTED LEDS FOR A SURFACE OF A VEHICLE

(71) Applicant: Ford Global Technologies, LLC, Dearborn, MI (US)

(72) Inventors: Patrick Kevin Holub, Novi, MI (US); John Robert Van Wiemeersch, Novi, MI (US); Stuart C. Salter, White Lake, MI (US)

(73) Assignee: Ford Global Technologies, Inc., Dearborn, MI (US)

( * ) Notice: Subject to any disclaimer, the term of this patent is extended or adjusted under 35 U.S.C. 154(b) by 215 days.

This patent is subject to a terminal disclaimer.

(21) Appl. No.: 14/735,468

(22) Filed: Jun. 10, 2015

(65) Prior Publication Data

US 2015/0273093 A1    Oct. 1, 2015

Related U.S. Application Data

(63) Continuation-in-part of application No. 14/603,636, filed on Jan. 23, 2015, now Pat. No. 9,573,517, which is a continuation-in-part of application No. 14/086,442, filed on Nov. 21, 2013.

(51) Int. Cl.
| | | |
|---|---|---|
| *A61L 2/10* | (2006.01) | |
| *H05B 37/02* | (2006.01) | |
| *B60Q 3/68* | (2017.01) | |
| *B60Q 3/20* | (2017.01) | |

(Continued)

(52) U.S. Cl.
CPC .................... *A61L 2/10* (2013.01); *A61L 9/20* (2013.01); *B60Q 3/20* (2017.02); *B60Q 3/68* (2017.02); *B60Q 3/80* (2017.02); *H05B 37/0218* (2013.01); *H05B 37/0227* (2013.01); *Y02B 20/46* (2013.01)

(58) Field of Classification Search
CPC .............. F21Y 2115/20; F21Y 2115/10; F21Y 2101/02; A61L 2/10; A61L 19/20; B60Q 3/68

See application file for complete search history.

(56) References Cited

U.S. PATENT DOCUMENTS

| | | |
|---|---|---|
| 5,053,930 A | 10/1991 | Benavides |
| 5,709,453 A | 1/1998 | Krent et al. |
| 5,839,718 A | 11/1998 | Hase et al. |

(Continued)

FOREIGN PATENT DOCUMENTS

| | | |
|---|---|---|
| CN | 201169230 Y | 2/2009 |
| CN | 201193011 Y | 2/2009 |

(Continued)

*Primary Examiner* — Robert May
(74) *Attorney, Agent, or Firm* — Vichit Chea; Price Heneveld LLP

(57) ABSTRACT

A self-disinfecting surface covering for a vehicle is disclosed. The surface covering comprising a pair of electrodes substantially conforms to a vehicle panel. A plurality of printed LEDs suspended in a semiconductor ink are printed between the electrodes and configured to emit a disinfecting emission. An outer layer of the surface covering is disposed proximate one of the electrodes. The outer layer is operable to transmit at least a portion of the disinfecting emission therethrough.

20 Claims, 5 Drawing Sheets

(51) Int. Cl.
   *B60Q 3/80*   (2017.01)
   *A61L 9/20*   (2006.01)

(56) References Cited

U.S. PATENT DOCUMENTS

| | | | |
|---|---|---|---|
| 6,031,511 | A | 2/2000 | DeLuca et al. |
| 6,117,362 | A | 9/2000 | Yen et al. |
| 6,419,854 | B1 | 7/2002 | Yocom et al. |
| 6,494,490 | B1 | 12/2002 | Trantoul |
| 6,577,073 | B2 | 6/2003 | Shimizu et al. |
| 6,729,738 | B2 | 5/2004 | Fuwausa et al. |
| 6,737,964 | B2 | 5/2004 | Samman et al. |
| 6,773,129 | B2 | 8/2004 | Anderson, Jr. et al. |
| 6,820,888 | B1 | 11/2004 | Griffin |
| 6,851,840 | B2 | 2/2005 | Ramamurthy et al. |
| 6,859,148 | B2 | 2/2005 | Miller |
| 6,871,986 | B2 | 3/2005 | Yamanaka et al. |
| 6,953,536 | B2 | 10/2005 | Yen et al. |
| 6,990,922 | B2 | 1/2006 | Ichikawa et al. |
| 7,161,472 | B2 | 1/2007 | Strumolo et al. |
| 7,213,923 | B2 | 5/2007 | Liu et al. |
| 7,216,997 | B2 | 5/2007 | Anderson, Jr. |
| 7,264,366 | B2 | 9/2007 | Hulse |
| 7,264,367 | B2 | 9/2007 | Hulse |
| 7,441,914 | B2 | 10/2008 | Palmer et al. |
| 7,501,749 | B2 | 3/2009 | Takeda et al. |
| 7,575,349 | B2 | 8/2009 | Bucher et al. |
| 7,635,212 | B2 | 12/2009 | Seidler |
| 7,745,818 | B2 | 6/2010 | Sofue et al. |
| 7,753,541 | B2 | 7/2010 | Chen et al. |
| 7,834,548 | B2 | 11/2010 | Jousse et al. |
| 7,862,220 | B2 | 1/2011 | Cannon et al. |
| 7,987,030 | B2 | 7/2011 | Flores et al. |
| 8,016,465 | B2 | 9/2011 | Egerer et al. |
| 8,022,818 | B2 | 9/2011 | Ia Tendresse et al. |
| 8,066,416 | B2 | 11/2011 | Bucher |
| 8,071,988 | B2 | 12/2011 | Lee et al. |
| 8,097,843 | B2 | 1/2012 | Agrawal et al. |
| 8,136,425 | B2 | 3/2012 | Bostick |
| 8,163,201 | B2 | 4/2012 | Agrawal et al. |
| 8,168,963 | B2 | 5/2012 | Ratcliffe |
| 8,178,852 | B2 | 5/2012 | Kingsley et al. |
| 8,197,105 | B2 | 6/2012 | Yang |
| 8,203,260 | B2 | 6/2012 | Li et al. |
| 8,207,511 | B2 | 6/2012 | Bortz et al. |
| 8,232,533 | B2 | 7/2012 | Kingsley et al. |
| 8,247,761 | B1 | 8/2012 | Agrawal et al. |
| 8,286,378 | B2 | 10/2012 | Martin et al. |
| 8,408,766 | B2 | 4/2013 | Wilson et al. |
| 8,415,642 | B2 | 4/2013 | Kingsley et al. |
| 8,421,811 | B2 | 4/2013 | Odland et al. |
| 8,466,438 | B2 | 6/2013 | Lambert et al. |
| 8,519,359 | B2 | 8/2013 | Kingsley et al. |
| 8,519,362 | B2 | 8/2013 | Labrot et al. |
| 8,552,848 | B2 | 10/2013 | Rao et al. |
| 8,606,430 | B2 | 12/2013 | Seder et al. |
| 8,624,716 | B2 | 1/2014 | Englander |
| 8,631,598 | B2 | 1/2014 | Li et al. |
| 8,664,624 | B2 | 3/2014 | Kingsley et al. |
| 8,683,722 | B1 | 4/2014 | Cowan |
| 8,724,054 | B2 | 5/2014 | Jones |
| 8,754,426 | B2 | 6/2014 | Marx et al. |
| 8,773,012 | B2 | 7/2014 | Ryu et al. |
| 8,846,184 | B2 | 9/2014 | Agrawal et al. |
| 8,876,352 | B2 | 11/2014 | Robbins et al. |
| 8,952,341 | B2 | 2/2015 | Kingsley et al. |
| 9,006,751 | B2 | 4/2015 | Kleo et al. |
| 9,018,833 | B2 | 4/2015 | Lowenthal et al. |
| 9,057,021 | B2 | 6/2015 | Kingsley et al. |
| 9,065,447 | B2 | 6/2015 | Buttolo et al. |
| 9,187,034 | B2 | 11/2015 | Tarahomi et al. |
| 9,299,887 | B2 | 3/2016 | Lowenthal et al. |
| 2002/0159741 | A1 | 10/2002 | Graves et al. |
| 2002/0163792 | A1 | 11/2002 | Formoso |
| 2003/0167668 | A1 | 9/2003 | Fuks et al. |
| 2003/0179548 | A1 | 9/2003 | Becker et al. |
| 2004/0213088 | A1 | 10/2004 | Fuwausa |
| 2006/0087826 | A1 | 4/2006 | Anderson, Jr. |
| 2006/0097121 | A1 | 5/2006 | Fugate |
| 2007/0032319 | A1 | 2/2007 | Tufte |
| 2007/0285938 | A1 | 12/2007 | Palmer et al. |
| 2007/0297045 | A1 | 12/2007 | Sakai et al. |
| 2009/0219730 | A1 | 9/2009 | Syfert et al. |
| 2009/0251920 | A1 | 10/2009 | Kino et al. |
| 2009/0260562 | A1 | 10/2009 | Folstad et al. |
| 2009/0262515 | A1 | 10/2009 | Lee et al. |
| 2009/0322202 | A1* | 12/2009 | Auday .............. B32B 17/10761 313/484 |
| 2011/0012062 | A1 | 1/2011 | Agrawal et al. |
| 2012/0001406 | A1 | 1/2012 | Paxton et al. |
| 2012/0104954 | A1 | 5/2012 | Huang |
| 2012/0183677 | A1 | 7/2012 | Agrawal et al. |
| 2012/0280528 | A1 | 11/2012 | Dellock et al. |
| 2013/0045132 | A1 | 2/2013 | Tumanov |
| 2013/0335994 | A1 | 12/2013 | Mulder et al. |
| 2014/0029281 | A1 | 1/2014 | Suckling et al. |
| 2014/0065442 | A1 | 3/2014 | Kingsley et al. |
| 2014/0103258 | A1 | 4/2014 | Agrawal et al. |
| 2014/0183377 | A1 | 7/2014 | Bettles et al. |
| 2014/0264396 | A1 | 9/2014 | Lowenthal et al. |
| 2014/0266666 | A1 | 9/2014 | Habibi |
| 2014/0373898 | A1 | 12/2014 | Rogers et al. |
| 2015/0046027 | A1 | 2/2015 | Sura et al. |
| 2015/0109602 | A1 | 4/2015 | Martin et al. |
| 2015/0138789 | A1 | 5/2015 | Singer et al. |
| 2015/0267881 | A1 | 9/2015 | Salter et al. |
| 2016/0016506 | A1 | 1/2016 | Collins et al. |
| 2016/0030609 | A1* | 2/2016 | Peterson ................ A61L 2/08 362/84 |
| 2016/0236613 | A1 | 8/2016 | Trier |

FOREIGN PATENT DOCUMENTS

| | | |
|---|---|---|
| CN | 204127823 U | 1/2015 |
| DE | 29708699 U1 | 7/1997 |
| DE | 10319396 A1 | 11/2004 |
| EP | 2668964 A1 | 12/2013 |
| EP | 2778209 A1 | 9/2014 |
| JP | 2000159011 A | 6/2000 |
| KR | 20060026531 A | 3/2006 |
| WO | 2006047306 A1 | 5/2006 |
| WO | 2014068440 A1 | 5/2014 |

* cited by examiner

US 9,782,504 B2

SELF-DISINFECTING SURFACE WITH PRINTED LEDS FOR A SURFACE OF A VEHICLE

CROSS-REFERENCE TO RELATED APPLICATIONS

This application is a continuation-in-part of U.S. Pat. No. 9,573,517, filed Jan. 23, 2015, and entitled "DOOR ILLUMINATION AND WARNING SYSTEM," which is a continuation-in-part of U.S. patent application Ser. No. 14/086,442, filed Nov. 21, 2013, and entitled "VEHICLE LIGHTING SYSTEM WITH PHOTOLUMINESCENT STRUCTURE." The aforementioned related applications are hereby incorporated by reference in their entirety.

FIELD OF THE INVENTION

The present disclosure generally relates to disinfecting systems, and more particularly, to disinfecting systems having thin profiles that may be operable to conform to non-planar surfaces.

BACKGROUND OF THE INVENTION

Disease and infection may be spread through indirect contact via various surfaces, which may correspond to touch surfaces that are commonly contacted. The disinfection of such surfaces may help prevent the spread of disease and infection to reduce associated health risks. The disclosure provides for various systems and apparatuses that may be utilized to disinfect various surfaces. At least one example of such surfaces may correspond to an automotive vehicle. The disclosure provides for disinfecting systems and apparatuses operable to disinfect various surfaces, which may correspond to surfaces that are commonly touched by vehicle occupants.

SUMMARY OF THE INVENTION

According to one aspect of the present disclosure, an apparatus configured to disinfect a surface of a vehicle is disclosed. The apparatus comprises a first electrode substantially conforming to a vehicle panel. A plurality of light emitting diodes (LEDs) suspended in a semiconductor ink are printed on the first electrode and configured to emit a disinfecting emission. A second electrode is in electrical connection with the plurality of LEDs and is configured to form a circuit via the first electrode such that a controller is operable to selectively activate the plurality of LEDs. An outer layer forming the surface is in connection with the second electrode. The outer layer is operable to transmit at least a portion of the disinfecting emission therethrough such that an outer surface of the outer layer is disinfected by the disinfecting emission.

According to another aspect of the present disclosure, a self-disinfecting surface covering for a vehicle is disclosed. The surface covering comprises a base layer and a pair of electrodes substantially conforming thereto. A plurality of printed LEDs are suspended in a semiconductor ink between the electrodes and configured to emit a disinfecting emission. An outer layer forming the surface covering is in connection with one of the pair of electrodes. The outer layer is operable to transmit at least a portion of the disinfecting emission therethrough such that an outer surface of the outer layer is disinfected by the disinfecting emission.

According to yet another aspect of the present disclosure, a formed, self-disinfecting surface covering for a vehicle is disclosed. The surface covering comprising a pair of electrodes substantially conforming to a vehicle panel. A plurality of printed LEDs suspended in a semiconductor ink are printed between the electrodes and configured to emit a disinfecting emission. An outer layer forming the surface covering is disposed proximate one of the electrodes. The outer layer is operable to transmit at least a portion of the disinfecting emission therethrough.

These and other aspects, objects, and features of the present disclosure will be understood and appreciated by those skilled in the art upon studying the following specification, claims, and appended drawings.

DETAILED DESCRIPTION OF THE PREFERRED EMBODIMENTS

As required, detailed embodiments of the present disclosure are disclosed herein. However, it is to be understood that the disclosed embodiments are merely exemplary of the disclosure that may be embodied in various and alternative forms. The figures are not necessarily to a detailed design and some schematics may be exaggerated or minimized to show function overview. Therefore, specific structural and functional details disclosed herein are not to be interpreted as limiting, but merely as a representative basis for teaching one skilled in the art to variously employ the present disclosure.

As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

The following disclosure describes a disinfecting apparatus. The disinfecting apparatus may be utilized for various surfaces that may correspond to surfaces that are commonly contacted. Such surfaces may include, but are not limited to door handles, hand rails, arm rests, work surfaces (e.g. tables, support surfaces), sanitary fixtures (e.g. toilet seats, faucets, faucet handles), and a variety of additional surfaces that may be contacted throughout their ordinary use. In an exemplary embodiment, the disinfecting apparatus may correspond to a vehicle fixture.

The disinfecting apparatus may correspond to a thin, flexible assembly, which may be utilized in a variety of applications. For the purposes of this disclosure, a vehicle fixture may refer to any interior or exterior piece of vehicle equipment, or part thereof, suitable for receiving various implementations of the apparatus described herein. While the implementations of the disinfecting apparatus described herein are primarily directed to automotive vehicle use, it should be appreciated that the apparatus or system may also be implemented in a variety of types of surfaces. Additionally, though automotive vehicles are depicted herein, the disinfecting apparatus may be utilized in other types of vehicles designed to transport one or more passengers such as, but not limited to, watercraft, trains, and aircraft.

Figure 1:
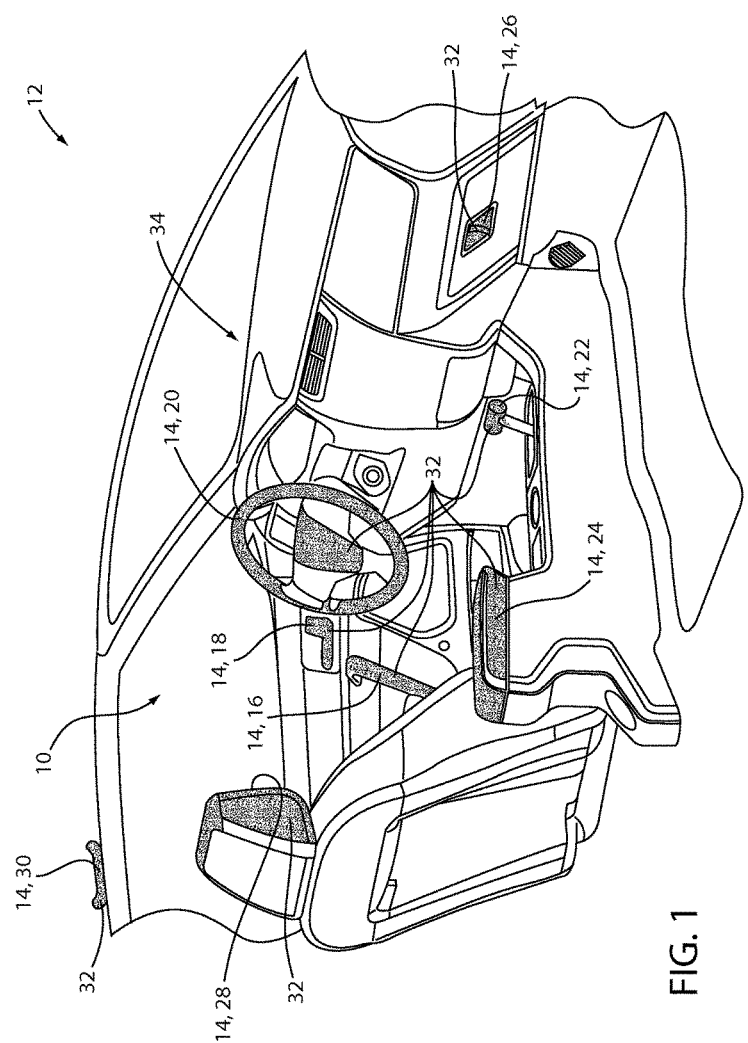
FIG. 1 is a perspective view of a passenger compartment of an automotive vehicle having at least one self-disinfecting surface.

Referring to FIG. 1, a passenger compartment 10 of an automotive vehicle 12 is generally shown having a variety of touch surfaces 14. The touch surfaces 14 may correspond to areas of the vehicle 12, typically interior, that are commonly contacted by passengers. Examples of touch surfaces 14 may include a passenger door handle 16, a door latch 18, a steering wheel 20, a shift knob 22, an arm rest 24, a console lever 26, a headrest 28, an exterior entry handle 30, etc. For purposes of illustration, each of the touch surfaces 14 may be configured to receive a self-disinfecting surface covering 32 (hereinafter surface covering 32). Each of the surface coverings 32 may correspond to one or more disinfecting apparatuses 34 configured to emit at least one wavelength of light configured to disinfect at least one of the touch surfaces 14 of the vehicle 12. The disinfecting apparatus 34 may be disposed in various locations in the vehicle and is designated generally as numeral 34.

The touch surfaces 14 may correspond to surfaces of various fixtures of the vehicle 12. Each of the surface coverings 32 may be molded to the fixtures, bonded to the surface of the fixtures, or affixed to the surfaces by other suitable means. Each of surface coverings 32 may be configured to be selectively activated by a controller 102 of the one or more disinfecting apparatuses 34 independently or in combination to at least partially disinfect the touch surfaces 14. Additionally, in some implementations, the surface covering 32 may be configured to emit an output emission corresponding to light in the visible spectrum. In this way, one or more of the surface coverings 32 may be configured to illuminate at least a portion of the passenger compartment 10 of the vehicle 12 as well as disinfect the touch surfaces 14. The controller 102 of the disinfecting apparatus 34 and a vehicle control module 104 in communication with the controller 102 are further discussed in reference to FIG. 5.

The surface coverings 32 may conform to various shapes and sizes of the touch surfaces 14 and may correspond to portions of a fixture having planar and/or non-planar configurations. For example, in an exemplary embodiment, the surface coverings 32 may have a thin profile and be of flexible materials providing for the assembly to conform to non-planar surfaces. Although exemplary fixtures are discussed herein, it should be appreciated that other fixtures may be used in accordance with the disinfecting apparatus 34 described herein. Such fixtures may include instrument panels and components thereon, interactive mechanisms (e.g. push buttons, switches, dials, touchscreens, and the like), printed surfaces, and various interior and/or exterior portions of the vehicle 12, which may be of metallic, polymeric, or a variety of materials.

As previously discussed, the surface covering 32 may be in communication with a controller 102. In some implementations, the controller 102 may further be in communication with a vehicle control module 104. The vehicle control module 104 may provide signals to the controller 102 in response to various user inputs, vehicle operating information, vehicle status information, etc. In response to one or more signals received from the vehicle control module 104, the controller 102 of the disinfecting apparatus 34 is operable to control one or more of the surface coverings 32 to significantly disinfect corresponding touch surfaces 14 of the vehicle 12. Further details regarding the controller 102 and the vehicle control module 104 are discussed in reference to FIG. 5. Though the disinfecting apparatus 34 and surface coverings 32 discussed herein are described as being in communication with the controller 102, one or more of the surface coverings 32 may be controlled by various forms of switches and/or analog or digital circuitry.

Figure 2:
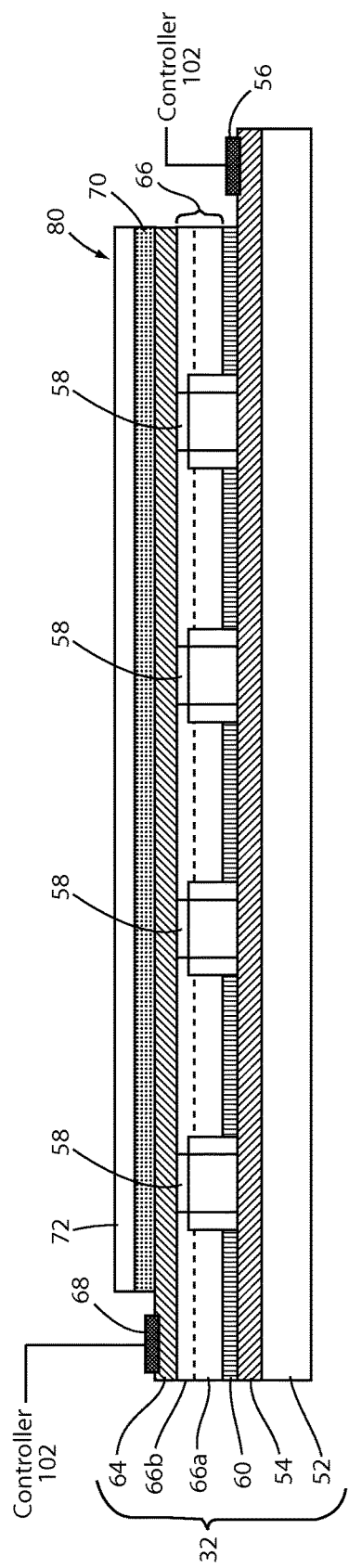
FIG. 2 is a detailed side view of a light producing assembly comprising a photoluminescent layer.

Referring to FIG. 2, the at least one surface covering 32 of the disinfecting apparatus 34 may correspond to a thin-film comprising a printed light-emitting diode (LED) assembly. The surface covering 32 may comprise a substrate 52. The substrate 52 may be opaque, transparent, or semi-transparent and may be thin having a flexible structure configured to attach and conform to a surface of a vehicle fixture. The surface covering 32 may be utilized in a variety of applications, which may require a thin overall thickness. The substrate 52 may be of a polymer, for example polycarbonate, poly-methyl methacrylate (PMMA), polyethylene terephthalate (PET), etc. In some embodiments, the substrate 52 may be dispensed from a roll to provide for integration into assembly operations for the surface covering 32 and may be approximately 0.1 mm to 2 mm in thickness. In an exemplary implementation, the surface covering 32 may be less than 1 mm in thickness and in some implementations, may be less than 0.6 mm in thickness.

A first electrode 54 may correspond to a cathodic conductive layer (hereinafter cathode 54) may be disposed on the substrate 52. The cathode 54 and/or various electrodes or conductive layers discussed herein may comprise a conductive epoxy, such as a silver-containing or copper-containing epoxy. The cathode 54 is conductively connected to a first bus bar or a cathodic bus bar 56. The cathodic bus bar 56 and other bus bars or conduits discussed herein may be of metallic and/or conductive materials which may be screen printed on the electrodes or conductive layers. Bus bars may be utilized in the surface covering 32 to conductively connect a plurality of light-emitting diode (LED) sources 58 to a power source via controller 102. In this way, the cathodic bus bar 56, and other bus bars utilized in the surface covering 32, may be configured to deliver electrical current substantially uniformly along and/or across the cathode 54 and other conductive layers in surface covering 32.

The LED sources 58 may be printed, dispersed or otherwise applied to the cathode 54 via a semiconductor ink 60. The LED sources 58 may be dispersed in a random or controlled fashion within the semiconductor ink 60. The LED sources 58 may correspond to micro-LEDs of gallium nitride elements, which may be approximately 5 microns to 400 microns in width substantially aligned perpendicular to the surface of the cathode 54. The semiconductor ink 60 may include various binding and dielectric materials including but not limited to one or more of gallium, indium, silicon carbide, phosphorous and/or translucent polymeric binders. In this configuration, the semiconductor ink 60 may contain various concentrations of LED sources 58 such that a dispersion density of the LED sources 58 may be adjusted for various applications.

The semiconductor ink 60 can be applied through various printing processes, including ink jet and silk screen processes to selected portion(s) of the substrate 52. The semiconductor ink 50 is applied such that the LED light sources 58 may form a circuit between the cathode 54 and a second electrode 64 or anodic conductive layer (hereinafter anode 64). More specifically, it is envisioned that the LED sources 58 are dispersed within the semiconductor ink 60, and shaped and sized such that a substantial quantity of them preferentially align perpendicular to the cathode 54 and the anode 64 during deposition of the semiconductor ink 60. The portion of the LED sources 58 that ultimately are electrically connected to the electrodes 54, 64 may be illuminated by a voltage source applied across the cathode 54 and the anode 64. Additional information regarding the construction of a light producing assembly configured to emit light at different wavelengths than the disinfecting apparatus 34 is disclosed in U.S. Pat. No. No. 9,299,887 to Lowenthal et al., entitled "ULTRA-THIN PRINTED LED LAYER REMOVED FROM SUBSTRATE," filed Mar. 12, 2014, the entire disclosure of which is incorporated herein by reference.

Though discussed in the particular embodiments as the cathode 54 and the anode 64, the first electrode 54 and the second electrode 64 may correspond to an anode and a cathode, respectively, such that the polarity and corresponding direction of the LED sources may be reversed. In such implementations, the light emitted from the LED sources 58 may be directed toward the substrate 52. In such configurations, a reflective layer 53 may be disposed between the first electrode 54 (anode in this particular implementation) and the substrate such that a disinfecting emission is reflected by the reflective layer 53 outward from the substrate 52. The reflective layer may be of any substantially reflective material, for example a metallic reflective material.

At least one dielectric layer 66 may be printed over the LED sources 58 to encapsulate and/or secure the LED sources 58 in position. The at least one dielectric layer 66 may correspond to a first dielectric layer 66a and a second dielectric layer 66b, which may be of a transparent material. The anode 64 may correspond to a top transparent conductor layer printed over the dielectric layer 66 to electrically connect the electrodes 54, 64 via the LED sources 58. The anode 64 is conductively connected to a second bus bar or anodic bus bar 68. The bus bars 56, 68 may be utilized in the surface covering 32 to conductively connect a plurality of LED sources 58 to the power source via controller 102.

The bus bars 56, 68 may be printed along opposite edges of the electrodes 54, 64 and electrically terminate at anode and cathode terminals. Points of connection between the bus bars 56, 68 and controller 102 may be at opposite corners of each bus bar 56, 68 for uniform current distribution across the electrodes 54, 64. In an exemplary implementation, each of the electrodes 54, 64 may be of indium tin oxide (ITO) or similar conductive materials that are substantially light transmissive.

Figure 3:
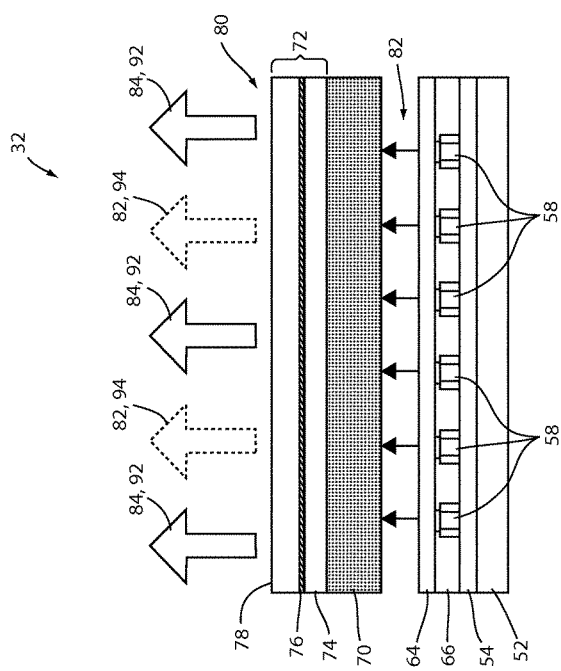
FIG. 3 is a side view of a light producing assembly demonstrating a photoluminescent layer configured to convert a wavelength of light.

Referring now to FIG. 2 and FIG. 3 in some implementations, a photoluminescent layer 70 may be applied to the anode 64. The photoluminescent layer 70 may be configured to convert a portion of a disinfecting emission 82 (e.g. ultraviolet light) emitted from the LED sources 58 to an output emission 84 corresponding to light in the visible spectrum. The photoluminescent layer 70 may have a limited concentration of a photoluminescent material such that a first portion 92 of the disinfecting emission 82 is converted to the output emission 84 and a second portion 94 of the disinfecting emission 82 is emitted from an outer surface 80 (e.g. the touch surface 14) of the surface covering 32. In this configuration, the output emission 84 may be emitted from the outer surface 80 to illuminate the surface covering in a visible light while the second portion 94 of the disinfecting emission 82 may pass through the photoluminescent layer 70 such that the outer surface 80 is disinfected by the disinfecting emission 82.

The photoluminescent layer 70 may be applied as a coating, layer, film, and/or photoluminescent substrate. The photoluminescent layer 70 may be applied by screen printing, flexography, and/or otherwise affixed to the anode 64. In various implementations, the LED sources 58 may be configured to emit a disinfecting emission 82 comprising a first wavelength corresponding to ultraviolet (UV) light. The LED sources 58 may be configured to emit the disinfecting emission 82 or an excitation emission into the photoluminescent layer 70 such that the photoluminescent material becomes excited. In response to the receipt of the disinfecting emission 82, the photoluminescent material converts a portion of the disinfecting emission 82 from the first wavelength to an output emission 84 comprising at least a second wavelength longer than the first wavelength.

The disinfecting emission 82 may be emitted from the LED sources 58, which may correspond to an ultraviolet light source. The LED sources 58 may be configured to emit the disinfecting emission 82 or excitation emission corresponding to a wavelength in the ultraviolet light range of approximately 10 nm to 400 nm. In an illustrative embodiment, the LED sources 58 may be configured to emit ultraviolet radiation in the range of approximately 10 nm to 400 nm and in some embodiments may emit radiation at approximately 200 nm to 300 nm, which may be suited particularly for disinfection.

An outer layer 72 of the surface covering 32 may correspond to one or more coatings configured to at least partially enclose the surface covering 32 and is at least partially UV and, optionally, visible light permeable. In some implementations, the outer layer 72 may correspond to a plurality of layers configured to provide a desired feel and appearance of the corresponding touch surface 14 of the vehicle 12. The outer layer 72 may correspond to one or more coatings or sealing layers applied to an exterior surface of the photoluminescent layer 70 or the anode 64. For example, the outer layer 72 may be applied to the anode 64 in implementations that do not incorporate the photoluminescent layer 70 for converting the first portion 92 of the disinfecting emission 82 to the output emission 84. The outer layer 72 may further be configured to protect the anode 64 and/or the photoluminescent layer 70 and various other portions of the assembly from damage and wear.

Referring now to FIG. 3, a detailed view of photoluminescent layer 70 and the outer layer 72 of the surface covering 32 are shown. As discussed herein, the photoluminescent layer 70 may be utilized in some embodiments to convert at least a portion of the disinfecting emission 82 to an output emission 84 in the visible light range. The LED sources 58 are in electrical communication with the electrodes 54, 64 and a power source via controller 102 such that the disinfecting emission 82 may be output from LED sources 58.

In an exemplary implementation, the disinfecting emission 82 may correspond to the excitation emission having a first wavelength corresponding approximately to an ultraviolet wavelength of light. The first wavelength may comprise a wavelength in the ultraviolet and near ultraviolet color range (~100-450 nm). In an exemplary implementation, the first wavelength may be approximately equal to 270 nm. Additionally, for embodiments incorporating the photoluminescent layer 70, specific photoluminescent materials may be selected such that the disinfecting emission 82 corresponds to the first wavelength configured which targets an absorption range of the specific photoluminescent materials. In this configuration, the photoluminescent material of the photoluminescent layer 70 may become excited in response to the receipt of the excitation emission and emit the output emission 84.

In embodiments that do not incorporate the photoluminescent layer 70, the disinfecting emission 82 may pass directly into the outer layer 72 and be emitted from the outer layer 72 having a wavelength substantially similar to that of the disinfecting emission 82. In embodiments that incorporate the photoluminescent layer 70, the disinfecting emission 82 may be transmitted into an at least partially UV light transmissive material of the photoluminescent layer 70. The disinfecting emission 82 is emitted from the LED sources 58 and may be configured such that the first wavelength corresponds to at least one absorption wavelength of one or more photoluminescent materials disposed in the photoluminescent layer 70. For example, the photoluminescent layer 70 may be configured to convert a portion of the disinfecting emission 82 at the first wavelength to an output emission 84 having a second wavelength, different from the first wavelength.

The photoluminescent layer 70 may comprise a specific concentration of photoluminescent material to ensure that only a portion of the disinfecting emission 82 is converted to the output emission 84. The output emission 84 may comprise one or more wavelengths, one of which may be longer than the first wavelength. The conversion of the disinfecting emission 82 to the output emission 84 may be referred to as a Stokes shift.

In some embodiments, the output emission 84 may correspond to a plurality of wavelengths. Each of the plurality of wavelengths may correspond to significantly different spectral color ranges. For example, the at least second wavelength of the output emission 84 may correspond to a plurality of wavelengths (e.g. second, third, etc.). In some implementations, the plurality of wavelengths may be combined in the output emission 84 to appear as substantially white light. The plurality of wavelengths may be generated by a red-emitting photoluminescent material having a wavelength of approximately 620-750 nm, a green emitting photoluminescent material having a wavelength of approximately 526-606 nm, and a blue or blue green emitting photoluminescent material having a wavelength longer than the first wavelength $\lambda_1$ and approximately 430-525 nm. In some implementations, a blue or blue green wavelength may correspond to the excitation emission being combined with the output emission 84. As discussed herein, a concentration of the photoluminescent material may be configured to allow at least a portion of the excitation emission to be emitted with the output emission 84 to add a blue hue to the output emission 84. The plurality of wavelengths may be utilized to generate a wide variety of colors of light from the each of the photoluminescent portions converted from the first wavelength. Though the particular colors of red, green, and blue are referred to herein, various photoluminescent materials may be utilized to generate a wide variety of colors and combinations to control the appearance of the output emission 84.

The photoluminescent materials, corresponding to the photoluminescent layer 70 may comprise organic or inorganic fluorescent dyes configured to convert the disinfecting emission 82 to the output emission 84. For example, the photoluminescent layer 70 may comprise a photoluminescent structure of rylenes, xanthenes, porphyrins, phthalocyanines, or other materials suited to a particular Stokes shift defined by an absorption range and an emission fluorescence. In some embodiments, the photoluminescent layer 70 may be of at least one inorganic luminescent material selected from the group of phosphors. The inorganic luminescent material may more particularly be from the group of Ce-doped garnets, such as YAG:Ce. As such, the photoluminescent materials may be selectively activated by the first wavelength received from the disinfecting emission 82 to emit the output emission 84 having a desired color.

Still referring to FIG. 3, the disinfecting apparatus 34 may further include the outer layer 72 in the form of the at least partially light permeable layer 74. In some implementations, the outer layer 72 may correspond to a plurality of layers configured to provide a desired feel and appearance of the corresponding touch surface 14 of the vehicle 12. The outer layer 72 may correspond to one or more coatings or sealing layers, which may be applied to an exterior surface of the photoluminescent layer 70 or the anode 64. The outer layer 72 may comprise at least one stability layer 76 configured to protect the photoluminescent material of the photoluminescent layer 70 from photolytic or thermal degradation and physical as well as chemical damage arising from environmental exposure. The stability layer 76 may be configured as a separate layer optically coupled and adhered to the photoluminescent layer 70. The stability layer 76 may also be integrated with the photoluminescent layer 70 and the outer layer 72.

The outer layer 72 may further comprise a contact layer 78, the outer surface of which corresponds to the touch surface 14 of the surface covering 32. The contact layer 78 may correspond to an at least partially light permeable material. The contact layer 78 of the outer layer 72 may correspond to a variety of materials, for example, an at least partially light transmissive polymeric material such as polypropylene. Polypropylene is a semi-crystalline polymer. The presence of this crystalline structure may enhance the stiffness, as well as the mechanical, chemical and thermal resistance of the material. Polypropylene normally crystallizes slowly and forms relatively large complex crystal aggregates known as spherulites. The growth of these spherulites is generally initiated around microscopic "sites" naturally present in the material.

A size of these spherulites is generally larger than the wavelength of visible light resulting in light scattering and hazing of the emissions transmitted through the outer layer 72 from the illumination apparatus. Adding a clarifier to polypropylene is equivalent to introducing "additional sites" in which spherulites can initiate their growth. As such, in some embodiments, the polypropylene may be clarified with a clarifier. By adding the clarifier, the rate of crystal initiation is increased throughout the polypropylene. This may provide for an increased number of crystals in the same amount of space provided by the smaller size of the crystals. The result of the smaller crystals is to allow light, such as the disinfecting emission 82 and/or the output emission 84, to pass through the outer layer 72. In some implementations, acrylic material and/or a flexible vinyl material may similarly be utilized for the overmolded portions.

In some implementations, the outer layer 72 may be integrated with the photoluminescent layer 70 and the stability layer 76 to form an integrated photoluminescent structure through sequential coating or printing of each layer, or by sequential lamination or embossing. Additionally, several layers may be combined by sequential coating, lamination, or embossing to form a substructure. The substructure may then be laminated or embossed to form the integrated photoluminescent structure. Once formed, the photoluminescent structure may be applied to the anode 64 such that the disinfecting emission 82 may be received from the LED sources 58 and converted to the output emission 84. Additional information regarding the construction of photoluminescent structures to be utilized in at least one photoluminescent portion of a vehicle is disclosed in U.S. Pat. No. 8,232,533 to Kingsley et al., entitled "PHOTOLYTICALLY AND ENVIRONMENTALLY STABLE MULTI-LAYER STRUCTURE FOR HIGH EFFICIENCY ELECTROMAGNETIC ENERGY CONVERSION AND SUSTAINED SECONDARY EMISSION," filed Jul. 31, 2012, the entire disclosure of which is incorporated herein by reference.

In some embodiments, the outer layer 72 may further comprise a colored layer applied to the surface covering 32 and configured to control or adjust an appearance of the outer surface 80 in an unilluminated state. The colored layer may comprise an at least partially light transmissible polymeric layer or coating that may be applied to the contact layer 78. The colored layer may be tinted any color to suit a desired appearance of the surface covering 32. In an exemplary embodiment, the photoluminescent material of the energy conversion layer may correspond to a red emitting rylene dye. Such a dye may cause the photoluminescent layer 70 to have a somewhat orange appearance. In such embodiments, the colored layer may be utilized to tint the surface covering 32 to a desired color, for example a neutral vehicle interior color such as grey, beige, etc.

Figure 4:
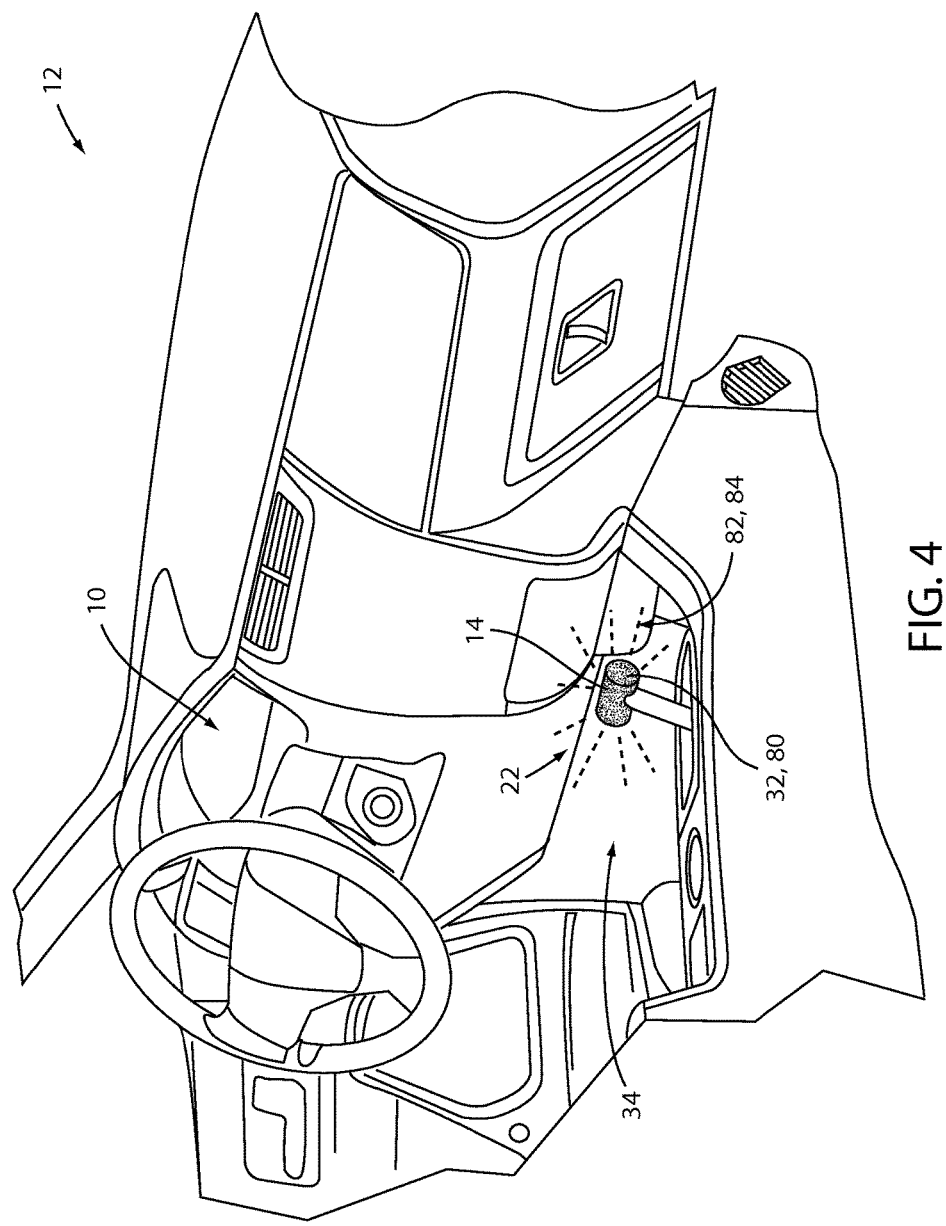
FIG. 4 is a detailed perspective view of a passenger compartment of an automotive vehicle having at least one self-disinfecting surface configured to provide illumination for the vehicle.

FIG. 4 demonstrates a detailed view of passenger compartment 10 of the vehicle 12 including the touch surface 14 of the shift knob 22. Referring now to FIGS. 3 and 4, as previously discussed herein, the disinfecting apparatus 34 may comprise the photoluminescent layer 70 incorporated in the surface covering 32. In such implementations, a first portion 92 of the disinfecting emission 82 may correspond to an excitation emission that has been converted by one or more photoluminescent materials of the photoluminescent layer 70 to emit the output emission 84. Additionally, a second portion 94 of the disinfecting emission 82 may pass through the photoluminescent layer 70 such that the outer surface 80 of the surface covering is substantially penetrated and infiltrated by the disinfecting emission 82. In this way, the outer surface 80 of the surface covering 32 may be illuminated by the output emission 84, and the outer surface 80 is also disinfected by the disinfecting emission 82/94 passing through the outer surface 80.

In some embodiments, the photoluminescent layer 70 may generate the output emission 84 to provide a visible notification that one or more of the surface coverings 32 are being disinfected. The brightness of the output emission 84 may be controlled by the concentration of the photoluminescent materials incorporated in the photoluminescent layer 70. The brightness may further be controlled by the duty cycle, voltage, density, and/or the type of LED sources 58 utilized in the surface covering 32. The first portion 92 and the second portion 94 of the disinfecting emission 82 may correspond to a ratio between the amount of light produced by the LED sources 58 and the concentration of the photoluminescent materials/types of photoluminescence utilized in the photoluminescent layer 70. For example, a high intensity output from the LED sources 58 may generate a large amount of the output emission 84 and a smaller amount of the second portion 94 of the disinfecting emission 82 if there is a relatively high concentration of photoluminescent material in the photoluminescent layer 70. Comparatively, a high intensity output from the LED sources 58 may generate a small amount of the output emission 84 and a larger amount of the second portion 94 of the disinfecting emission 82 if there is a relatively low concentration of photoluminescent material in the photoluminescent layer 70.

As described herein, the disinfecting surface covering 32 of the disinfecting apparatus 34 may provide for a system and method operable to disinfect a surface of a vehicle 12. Particularly, the disinfecting surface covering 32 may be utilized for common touch surfaces 14 that may gather contaminants and infectious organisms that may provide for the spread of disease in the vehicle 12. By selectively activating the LED sources 58 to emit the disinfecting emission 82, the disinfecting apparatus 34 may be operable to disinfect at least a portion of the outer surface 80 of the surface covering 32. In some embodiments, the photoluminescent layer 70 may be incorporated into or proximate the surface covering 32. In such configurations, the output emission 84 may also be output from the outer surface 80 such that the surface covering 32 is illuminated in visible light while disinfecting the outer surface 80.

Figure 5:
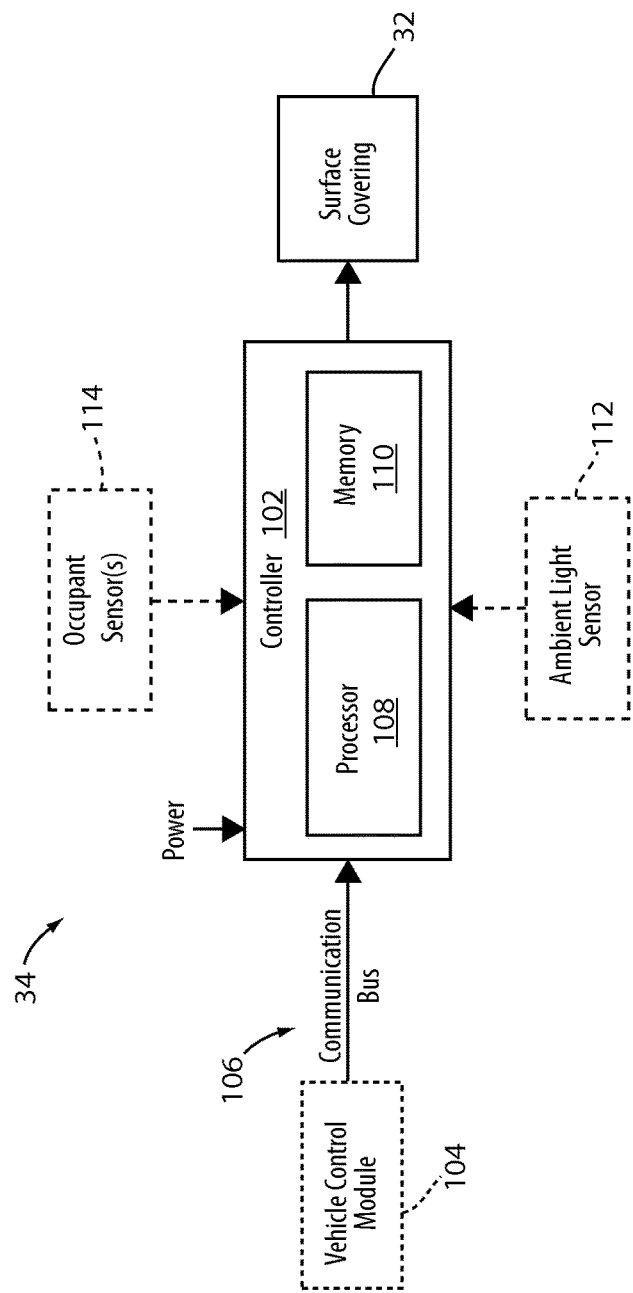
FIG. 5 is a block diagram of a lighting apparatus comprising a light producing assembly.

Referring to FIG. 5, a block diagram of the disinfecting apparatus 34 or system configured to control the LED light sources 58 of the surface covering 32 is shown. The disinfecting apparatus 34 comprises a controller 102 in communication with the LED sources 58 in surface covering 32 via the electrode terminals. The controller 102 may be in communication with the vehicle control module 104 via a communication bus 106 of the vehicle. The communication bus 106 may be configured to deliver signals to the controller 102 identifying various vehicle states. For example, the communication bus 106 may be configured to communicate to the controller 102 a drive selection of the vehicle, an ignition state, a door open or ajar status, a remote activation of the LED sources 58, or any other information or control signals that may be utilized to activate or adjust the disinfecting emission 82 of the surface covering 32. Though the controller 102 is discussed herein, in some embodiments, the disinfecting apparatus 34 may be activated in response to an electrical or electro-mechanical switch.

The controller 102 may comprise a processor 108 comprising one or more circuits configured to receive the signals from the communication bus 106 and transmit output signals to control the LED sources 58 to emit the disinfecting emission 82. The processor 108 may be in communication with a memory 110 configured to store instructions to control the activation of the LED sources 58. The controller 102 may further be in communication with an ambient light sensor 112. The ambient light sensor 112 may be operable to communicate a light condition, for example a brightness level or intensity of the ambient light proximate the vehicle 12. In response to the level of the ambient light, the controller 102 may be configured to adjust a light intensity output from the LED sources 58. The intensity of the light output from the LED sources 58 may be adjusted by controlling a duty cycle, current, or voltage supplied to the LED sources 58.

The controller 102 may further be in communication with one or more occupancy sensors 114 configured to detect the presence of a vehicle occupant. An occupancy sensor 114 may generally be configured to detect if a living occupant (e.g. an animal) is inside the vehicle 12. Occupancy sensors 114 may comprise various transducers and/or sensors, for example weight sensors in the passenger seats and/or floor (e.g. a seat sensor), proximity sensors, infrared sensors, cameras, microphones, and various devices that may be configured to detect weight, temperature, motion, sound, etc. in the passenger compartment 10 of the vehicle 12. The controller 102 may utilize signals received from the occupancy sensor 114 to identify whether an occupant is within the interior of the vehicle 12. Upon a determination that the vehicle 12 is unoccupied, the controller 102 may activate the LED sources 58 such that the surface covering 32 is disinfected.

In combination with communications received via the communication bus 106, the controller 102 may be operable to identify whether an occupant is within the passenger compartment 10 of the vehicle and additionally whether the interior of the vehicle 12 is secure (e.g. closures and windows of the vehicle are closed). In this configuration, the disinfecting apparatus 34 may be operable to control the disinfecting emission 82 to limit an exposure to occupants of the vehicle 12. The windows of the vehicle may comprise a UV filtering or blocking coating that may be operable to limit incoming UV radiation from the sun as well as preventing the disinfecting emission 82 from escaping the vehicle 12.

For the purposes of describing and defining the present teachings, it is noted that the terms "substantially" and "approximately" are utilized herein to represent the inherent degree of uncertainty that may be attributed to any quantitative comparison, value, measurement, or other representation. The term "substantially" and "approximately" are also utilized herein to represent the degree by which a quantitative representation may vary from a stated reference without resulting in a change in the basic function of the subject matter at issue.

Though discussed in various illustrative examples in reference to vehicle surfaces, the disinfecting apparatus may be utilized for various surfaces, other than vehicular, that may correspond to surfaces that are commonly contacted. Such surfaces may include, but are not limited to door handles, hand rails, arm rests, work surfaces (e.g. tables, support surfaces), sanitary fixtures (e.g. toilet seats, faucets, faucet handles), and a variety of additional surfaces that may be contacted throughout their ordinary use. It is to be understood that variations and modifications can be made on the aforementioned structure without departing from the concepts of the present invention, and further it is to be understood that such concepts are intended to be covered by the following claims unless these claims by their language expressly state otherwise.

What is claimed is:

1. An apparatus configured to disinfect a surface of a vehicle comprising:
   a first electrode substantially conforming to a vehicle panel;
   a plurality of printed LEDs suspended in a semiconductor ink on the first electrode and configured to emit a disinfecting emission;
   a second electrode in electrical connection with the plurality of LEDs; and
   an outer layer forming the surface in connection with the second electrode, wherein the outer layer is operable to transmit at least a portion of the disinfecting emission therethrough.

2. The apparatus according to claim 1, further comprising a controller in communication with the first electrode and the second electrode.

3. The apparatus according to claim 2, wherein the controller is configured to selectively activate the disinfecting emission in response to at least one state of the vehicle.

4. The apparatus according to claim 3, wherein the at least one state corresponds to the vehicle being unoccupied.

5. The apparatus according to claim 2, further comprising at least one occupancy sensor in communication with the controller.

6. The apparatus according to claim 5, wherein the at least one occupancy sensor corresponds to at least one of a seat sensor, a proximity sensor, an infrared sensor, a camera and a microphone.

7. The apparatus according to claim 1, further comprising a photoluminescent layer applied between the second electrode and the outer layer.

8. The apparatus according to claim 7, wherein the photoluminescent layer is configured to convert a portion of the disinfecting emission to an output emission.

9. The apparatus according to claim 8, wherein the output emission corresponds to light in the visible range configured to illuminate at least a portion of the vehicle.

10. A self-disinfecting surface covering for a vehicle comprising:
    a base layer;
    a pair of electrodes substantially conforming to the base layer;
    a plurality of LEDs suspended in a semiconductor ink between the electrodes configured to emit a disinfecting emission; and
    an outer layer of the surface covering which is in connection with one of the pair of electrodes, wherein the outer layer is operable to transmit at least a portion of the disinfecting emission therethrough.

11. The surface covering according to claim 10, wherein the surface covering forms a flexible, thin-film layer configured to conform to non-planar surfaces.

12. The surface covering according to claim 10, wherein the surface covering has a profile thickness of approximately 0.1 mm to 2 mm.

13. The surface covering according to claim 10, wherein the base layer comprises an attachment surface configured to conform to a surface of a panel of the vehicle.

14. The surface covering according to claim 10, where the disinfecting emission corresponds to a wavelength of light less than approximately 400 nm.

15. The surface covering according to claim 10, further comprising a photoluminescent layer applied between one of the electrodes and the outer surface.

16. The surface covering according to claim 15, wherein the photoluminescent layer is configured to convert a portion of the disinfecting emission to an output emission corresponding to at least one wavelength of light greater than approximately 400 nm.

17. A formed, self-disinfecting surface covering for a vehicle comprising:
    a pair of electrodes substantially conforming to a vehicle panel;
    a plurality of LEDs suspended in a semiconductor ink between the electrodes configured to emit a disinfecting emission; and
    an outer layer of the surface covering proximate one of the electrodes, wherein the outer layer is operable to transmit at least a portion of the disinfecting emission therethrough.

18. The surface covering according to claim 17, wherein the pair of electrodes corresponds to conductive layers having the printed LEDs applied via a printing process therebetween.

19. The surface covering according to claim 17, further comprising a photoluminescent layer applied between the pair of electrodes and the outer surface.

20. The surface covering according to claim 19, wherein the photoluminescent layer is configured to convert a portion of the disinfecting emission to an output emission corresponding to at least one wavelength of light having a length greater than approximately 400 nm.

* * * * *